(12) United States Patent
Huang

(10) Patent No.: US 10,548,853 B2
(45) Date of Patent: Feb. 4, 2020

(54) ONCOLYTIC VIRUS FORMULATION AND PREPARATION METHOD THEREOF

(71) Applicant: HUBEI SOUNDNY BIOTECHNOLOGY CO., LTD., Wuhan (CN)

(72) Inventor: Bo Huang, Wuhan (CN)

(73) Assignee: HUBEI SOUNDNY BIOTECHNOLOGY CO., LTD., Hubei (CN)

( * ) Notice: Subject to any disclaimer, the term of this patent is extended or adjusted under 35 U.S.C. 154(b) by 0 days.

(21) Appl. No.: 15/825,065

(22) Filed: Nov. 28, 2017

(65) Prior Publication Data

US 2018/0078508 A1 Mar. 22, 2018

Related U.S. Application Data

(63) Continuation of application No. PCT/CN2016/077927, filed on Mar. 30, 2016.

(30) Foreign Application Priority Data

May 29, 2015 (CN) .............................. 201510289636

(51) Int. Cl.
| | |
|---|---|
| *C12N 7/02* | (2006.01) |
| *A61K 35/76* | (2015.01) |
| *A61K 9/50* | (2006.01) |
| *C12N 7/00* | (2006.01) |
| *A61K 35/13* | (2015.01) |
| *A61K 35/761* | (2015.01) |

(52) U.S. Cl.
CPC ............ *A61K 9/5068* (2013.01); *A61K 35/13* (2013.01); *A61K 35/76* (2013.01); *A61K 35/761* (2013.01); *C12N 7/00* (2013.01); *C12N 7/02* (2013.01); *C12N 2720/12032* (2013.01); *C12N 2760/20232* (2013.01); *C12N 2760/20251* (2013.01)

(58) Field of Classification Search
CPC ...... A61K 9/5068; A61K 35/13; A61K 35/76; C12N 7/00; C12N 7/02
See application file for complete search history.

(56) References Cited

U.S. PATENT DOCUMENTS

2013/0236537 A1 9/2013 Huang
2013/0309270 A1* 11/2013 von Andrian .......... A61K 39/00
424/277.1

FOREIGN PATENT DOCUMENTS

| | | |
|---|---|---|
| CN | 102302784 A | 1/2012 |
| CN | 102471300 A | 5/2012 |
| CN | 103260650 A | 8/2013 |
| CN | 104822626 A | 8/2015 |
| CN | 104958324 A | 10/2015 |
| WO | WO 99/45783 A1 | 9/1999 |
| WO | WO 2014/131898 A1 | 4/2014 |

OTHER PUBLICATIONS

Mendez et al. (Biomaterials, 2014, vol. 35, pp. 9554-9561).*
Gyorgy et al. Journal of Biomaterials 2014, vol. 35 (26, pp. 7598-7609.*
Fizpatrick et al. Human Gene Therapy, 2014, vol. 25, pp. 785-786.*
Kamen, Amine et al., "Development and optimization of an adenovirus production process" The Journal of Gene Medicine, vol. 6; (Dec. 2004); pp. S184-S192.
International Search Report of corresponding International PCT Application No. PCT/CN2016/077927, dated Jun. 24, 2016.
Xu, Zun-You et al., "Cell-based Delivery of Oncolytic Viruses" China Journal of International Oncology; vol. 38, No. 10; (Oct. 2011); pp. 723-725.
The Chinese First Examination Report of corresponding China patent application No. 201510289636.7, dated May 29, 2018.
Cao, Yuchun et al., "Microparticles mediate human papillomavirus type 6 or 11 infection of human macrophages Infection of human macrophages" Cellular and Molecular Immunology, vol. 14, pp. 395-397 (2017), English Abstract is enclosed.
Gyorgy, Bence et al., "Naturally enveloped AAV vectors for shielding neutralizing antibodies and robust gene delivery in vivo" Biomaterials, vol. 35, Issue 26, (Aug. 2014), pp. 7598-7609, English Abstract is enclosed.
Kaneda, Yasufumi et al., "Current status of gene therapy in Japan and other countries" Japanese Journal of Clinical Medicine, vol. 68, Suppl 8, pp. 577-583, (Aug. 2010), English Abstract is enclosed.
Shimoyama, Satofumi et al., "Oncolytic viral therapy for cancer therapy" Nippon Rinsho. Japanese Journal of Clinical Medicine, vol. 64, Issue 3, pp. 589-596, (Apr. 2006).
Nakamura, Takafumi et al., "Oncolytic virotherapy" Nippon Rinsho. Japanese Journal of Clinical Medicine, vol. 67, Suppl 3, pp. 572-576, (2009), English Abstract is enclosed.
The Japanese Examination Report of corresponding Japan application No. 2018-513707, dated Dec. 3, 2018.

\* cited by examiner

*Primary Examiner* — Bao Q Li
(74) *Attorney, Agent, or Firm* — J.C. Patents

(57) ABSTRACT

The present invention provides an oncolytic virus formulation and preparation method thereof. The oncolytic virus formulation comprises cell vesicles derived from apoptotic tumor cells and oncolytic viruses coated in the cell vesicles as an effective component. The oncolytic virus formulation uses cell vesicles derived from tumor cells themselves to coat the oncolytic viruses, so as to evade the body's immune system attack and can be targeted to the tumor treatment site, and improve the tumor-killing effect.

2 Claims, 5 Drawing Sheets
(4 of 5 Drawing Sheet(s) Filed in Color)

ONCOLYTIC VIRUS FORMULATION AND PREPARATION METHOD THEREOF

CROSS-REFERENCE TO RELATED APPLICATIONS

This application is a continuation of International Application No. PCT/CN2016/077927, filed on Mar. 30, 2016, which claims priority to Chinese Patent Application No. 201510289636.7, filed on May 29, 2015. The disclosures of the aforementioned applications are hereby incorporated by reference in their entireties.

FIELD OF THE TECHNOLOGY

The invention relates to an oncolytic virus formulation and preparation method thereof, and more particularly relates to an oncolytic virus formulation and preparation method thereof.

BACKGROUND

Malignant tumors are diseases that seriously threaten human life and health, searching for an effective therapy with less toxic side effects has became the most important medical research in recent years. According to the principle of enantiopathy, using viruses to kill tumor cells is an ideal strategy for cancer treatment. However, this strategy faces two problems: how to make viruses selectively reach tumor site and how to make viruses escape from body's immune system attack.

Viral DNA or RNA is assembled with proteins and other biomolecules to form viral particle, which can infect tumor cell and replicate in large quantities in tumor cell to produce new virus particles and eventually cause lysis of the tumor cell, i.e. it is so-called oncolytic virus, i.e. tumor-killing virus capable of replicating. However, oncolytic viruses as alien components will be immunologically rejected by the body upon entry into the body, in particular, the production of antiviral antibodies can limit the antitumor effect of oncolytic viruses through clearance of the viruses. In addition, free oncolytic viruses easily access into normal tissues, which not only weaken the effective killing effect of viruses on tumor cells, but also cause damage to normal tissues, and generate toxic side effects.

SUMMARY

The present invention provides an oncolytic virus formulation, oncolytic viruses as a therapeutically effective component are coated in cell vesicles obtained from apoptotic tumor cells, and the oncolytic virus formulation can be used as a targeted biological agent for the treatment of tumor diseases and effectively promotes the tumor-killing effect of oncolytic viruses, and reduces toxic side effects on the body.

The present invention provides a method for preparing an oncolytic virus formulation, which realizes that oncolytic viruses as a therapeutically effective component are coated in cell vesicles derived from apoptotic tumor cells, and microparticles generated after cell vesicles coat oncolytic viruses are successfully collected, the microparticles are the oncolytic virus formulation of the present invention.

The present invention provides an oncolytic virus formulation, which is formed by using cell vesicles, produced from oncolytic viruses infecting tumor cells to induce apoptosis, as carriers to coat oncolytic viruses.

The oncolytic virus formulation provided by the present invention is formed by cell vesicles coating oncolytic viruses, which is used as a target biological agent to facilitate oncolytic viruses reach tumor treatment site so as to improve the antitumor effect while utilizes cell vesicles derived from tumor cells themselves to coat oncolytic viruses and allows the oncolytic viruses to evade the body's immune system attack.

As basic knowledge in the field, when a cell is subjected to a apoptosis signal or stimulation signal, local cell membrane structure changes, expands outward and coats cellular content, released to the outside of the cell in the form of cell vesicles, whose diameter is between 100-1000 nanometers (nm), that is the "cell vesicles" (i.e. microparticles) as described in this invention. In addition, at different stages of apoptosis a cell can also release apoptotic bodies with a diameter of 1-3 μm and exosomes with a diameter of 30-100 nm. There are significant differences between apoptotic bodies or exosomes and cell vesicles, which are not included in the present invention. Just because tumor cells will produce apoptotic bodies, exosomes and the like during the apoptosis process, the technical solution of the present invention requires specific steps and conditions to obtain an oncolytic virus formulation generated after cell vesicles coat oncolytic viruses.

The applicant of the present application has disclosed pharmaceutical preparations which use cellular vesicles to coat chemotherapy drugs so as to achieve targeted administration, specifically referred to CN102302784A. The technical solution of the present invention has different design and application characteristics than the technical solution of vesicles coating chemotherapy drugs. After enter tumor cells, chemotherapy drugs are coated by cell vesicles released from apoptotic tumor cells through the physical space wrapping principle to generate a micro-particle formulation loaded with chemotherapy drugs. In the technical solution of the present invention, an oncolytic virus enters into a tumor cell and undergoes a large amount of biosynthesis with raw materials such as amino acids, nucleotides and lipid molecules in the tumor cell. During this process, the virus is in an active state and has the ability of activity replication, and is able to interact with the cytoskeleton or cell membrane of the tumor cell, which eventually results in the tumor cell releasing vesicles and forming cell particles wherein oncolytic viruses are coated, the cell particles are also known as microparticles. It is different from coating chemotherapy drugs that only the number of oncolytic viruses and tumor cells reaches an appropriate ratio can facilitate to get a micro-particle formulation which has therapeutic effect, that is, too few oncolytic viruses cannot achieve the replication effect, too much oncolytic viruses cause tumor cells to die, and lead to a drastic reduction in the number of released vesicles. In addition, chemotherapy drug, as small molecular substance, typically has a particle size of less than 1 nm, while the diameter of a virus can be between 50-200 nm and the diameter of a cell vesicle is between 100-1000 nm, therefore, whether cell vesicles can coat viruses during release progress can not be easily deduced by its ability of coating chemotherapy drugs, only when viruses are copied to a certain number in tumor cells, the probability that cell vesicles coat viruses is increased and the number is increased. Therefore, compared with cell vesicles coating chemotherapy drugs, cell vesicles coating viruses needs to consider factors of viral biological replication and viral particle size.

According to the technical solution provided by the present invention, in order to obtain microparticles that cell vesicles effectively coat oncolytic viruses, a ratio of oncolytic viruses to tumor cells in the preparation system is preferably between 1:1 and 20:1. Further, the ratio may be 10:1.

The present invention provides a method for preparing an oncolytic virus formulation, which comprises mixing oncolytic viruses and tumor cells in a ratio of 1:1 to 20:1 so as to infect tumor cells, and culturing the infected tumor cells to induce apoptosis at 37° C. and 5% oxygen content, collecting microparticles released from the apoptotic tumor cells within 48-72 hours, wherein the microparticles are the oncolytic virus formulation generated after cell vesicles coat oncolytic viruses. In the technical solution of the present application, the ratio of oncolytic viruses to tumor cells refers to a quantity ratio.

Oncolytic virus used in the technical solution of the present invention can be any commercially available oncolytic virus. For example, the oncolytic virus is an oncolytic adenovirus. Adenovirus is a common virus for infecting humans, which has strong immunogenicity and can be rapidly cleared by the body's immune system, and is not integrated into genomic DNA molecules and do not cause genomic DNA mutation, therefore, the use of this virus has a very good safety.

Further, the tumor cells comprise cells of ovarian cancer, breast cancer, lung cancer, gastric cancer, colon cancer, liver cancer, pancreatic cancer or prostate cancer and the like.

In the technical solution of the present invention, as for the collection of microparticles, a supercentrifuge can be used for separation at low temperature or room temperature. In specific embodiment, the microparticles can be collected by a supercentrifuge at a low temperature (about 4° C.) and at a centrifugal force of 1000-50000 g. For example, tumor cells and their debris can be removed at a centrifugal force of not more than 5000 g, and the obtained precipitate collected at a centrifugal force of 10000 g-50000 g is the microparticles. Furthermore, tumor cells and their debris can be removed at a centrifugal force of not more than 5000 g, and the obtained precipitate collected at a centrifugal force of 10000 g is the microparticles.

An oncolytic virus formulation provided by the present invention includes cell vesicles derived from apoptotic tumor cells and oncolytic viruses which are coated in the cell vesicle and used as an effective component, the oncolytic virus formulation is prepared according to any one of the aforementioned methods.

An oncolytic virus formulation provided by the present invention becomes a kind of microparticles due to the use of the above-mentioned cell vesicles derived from apoptotic tumor cells as carriers for coating oncolytic viruses. In contrast to free oncolytic viruses, oncolytic viruses coated in cell vesicles cannot be recognized by immune system, so that they can reach tumor site safely and effectively. A common free oncolytic virus enters into a cell by the mediation of special receptor molecules on the cell membrane, however, some tumor cells themselves do not express the receptor or actively down-regulate the expression of the receptor, thus can avoid the invasion of oncolytic viruses. In the technical solution of the present application, however, since cell vesicles derived from tumor cells are extremely easy to fuse with the cell membrane of the tumor cells, oncolytic viruses coated in the cell vesicles are mediated to enter the tumor cells.

In the technical solution of the present invention, an oncolytic virus formulation generated from cell vesicles coating oncolytic viruses has a particle size of 100 to 1000 nm.

It can be seen that cell vesicles used for coating oncolytic viruses in the present invention cannot enter normal tissues through normal capillaries because the size of cell vesicles is much larger than the permeability (5-10 nm) of normal tissue capillaries, avoiding the toxic side effects, caused by the direct injection of free oncolytic viruses in the prior art, on other normal tissues of the body.

It is understood that the present invention provides a new idea and new technical solution to obtain targeted oncolytic virus formulation, the targeted oncolytic virus formulation can target different types of clinical malignancies such as ovarian cancer, breast cancer, lung cancer, gastric cancer, colon cancer, liver cancer, pancreatic cancer and prostate cancer. Cell vesicles (carriers) used to coat oncolytic viruses are preferably derived from tumor cells of the same type as patient's tumor or cells of other types which are capable of making oncolytic viruses replicate.

Oncolytic viruses infecting tumor cells and inducing the apoptosis of tumor cells as described in the present invention, can be judged by the criteria well-known to those skilled in the art, for example, if the tumor cells become smaller and dimmer through observation, the cells are considered to be apoptotic cells.

In the technical solution provided by the present invention, before oncolytic viruses infect tumor cells, the method further comprises culturing the tumor cells. Methods for culturing the above-mentioned cells can be conventional culturing methods in the art.

Those skilled in the art can prepare an oncolytic virus formulation according to conventional methods, especially an injection formulation. For example, injection liquid, which can be produced by suspending the collected microparticles with physiological saline.

An oncolytic virus formulation of the present invention may be a unit formulation. The unit formulation refers to a formulation which can provide active ingredient in an amount required for a single administration, such as one unit (one needle of) injection. The amount of pharmaceutical required for a single administration to patient can be easily calculated by multiplying patient's body weight by dose per unit of body weight of the patient. For example, during the preparation of pharmaceuticals, adult body weight is generally assumed as 50-70 kg, and using it to calculate the amount of pharmaceutical required for a single administration to patient. Dose per unit body weight of experimental animal and human may be calculated by an equivalent dose conversion relationship. For example, effective dose for human can be derived from the dose for experimental animal according to an equivalent dose conversion relationship between experimental animals and human that well-known for an ordinary skilled in the art (see, for example, guidances of FDA, SFDA and other drug regulatory authorities, or HUANG Jihan, et al., equivalent dose conversion between different animals and between animal and human in pharmacological experiment, Chinese Journal of Clinical Pharmacology and Therapeutics, 2004 September; 9 (9): 1069-1072). In embodiments of the present invention, it can use body surface area conversion factor 0.0026 for human and mouse to derive dose for human from mouse.

Furthermore, according to a mouse experiment by the applicant, the unit formulation of an oncolytic virus formulation for human may comprise $1\times10^7$-$1\times10^8$ of microparticles.

The present invention also provides a method for treating or preventing tumors, which comprises a process of administering said oncolytic virus formulation to an individual having a tumor or to an individual having a tendency to develop a tumor.

The technical solution of the present invention has the following technical effects:

1. The preparation method provided by the present invention can obtain microparticles, formed after cell vesicles coat oncolytic viruses, that is an oncolytic virus formulation, rather than exosomes or apoptotic bodies; by regulating the dose of oncolytic viruses used, more than 95% of cell vesicles are able to coat oncolytic viruses, so that an oncolytic virus formulation of the present application can be obtained efficiently.

2. Cell vesicles derived from apoptotic tumor cells are taken as carriers of oncolytic viruses of the present invention, so that the attack of immune system to oncolytic viruses when they enter body is avoided, and it is more benefit for oncolytic viruses to reach tumor treated position, and the effect of killing tumor is improved.

3. In the technical solution of the present application, due to the use of cell vesicles derived from tumor cells as carriers, oncolytic viruses coated therein can easily enter tumor cells.

4. Microparticles which coat oncolytic viruses in the present invention can not enter normal tissues through normal capillaries because the size of microparticles is much larger than the permeability (5-10 nm) of normal tissue capillaries, avoid the toxic side effects on other normal tissues of the body caused by the direct injection of free oncolytic virus.

5. Tumor cells have indefinite proliferation characteristics, and their culture methods are well-developed, according to the technical solution described in the present invention, a large number of cell vesicles can be obtained from tumor cells to prepare an oncolytic virus formulation, and the cost is low and the operation is simple.

BRIEF DESCRIPTION OF THE DRAWINGS

This application contains at least one drawing executed in color. Copies of this patent or patent application publication with color drawing(s) will be provided by the office upon request and payment of the necessary fee.

In FIG. 1b, y-axis represents the number density of particles in a microparticle sample to be measured, the value of x-axis corresponding to the red curve peak represents the diameter range for most of the microparticles in the sample.

DETAILED DESCRIPTION

In order to confirm that tumor cell-derived cell vesicles are capable of coating oncolytic adenoviruses, effectively killing tumor cells and having no obvious toxic side effects in vivo, the present invention is further described as below with reference to drawings and the examples.

Various tumor cells, oncolytic adenoviruses and test animals used in the following examples:

A2780 human ovarian cancer cell line, MCF-7 human breast cancer cell line, A549 human lung cancer cell line, SNU1 human gastric cancer cell line, Caco2 human colon cancer cell line, HepG2 human hepatoma cell line, ASCP-1 human pancreatic cancer cell line, LINCap human prostate cancer cell lines, all are commercially available from American ATCC Center or from China Center for Type Culture Collection (CCTCC).

Oncolytic adenoviruses are available from Shanghai Sanwei Biotechnology Co., Ltd., have the name of recombinant human type 5 adenovirus (H101). 200 female nude mice, each weighing 18 grams, and are purchased from the Experimental Animal Center of the Chinese Academy of Medical Sciences and Peking Union Medical College.

Example 1: Oncolytic Adenoviruses were Used to Induce Apoptosis of Human Lung Cancer Cells to Produce Microparticles 1. Experimental Steps A549 human lung cancer cells were cultured in DMEM cell culture fluid, so that the number of cells reached $1\times10^7$; $1\times10^8$ oncolytic adenoviruses were added to the culture fluid to infect human lung cancer cells; at 37° C. and 5% oxygen content, the infected tumor cells were cultured; at 48th hour after administration of oncolytic adenoviruses, when the tumor cells became smaller and dimmer, the supernatant of the human lung cancer cell culture fluid was centrifuged successively at the centrifugal force of 1000 g and 5000 g for each 10 minutes, the cells and debris were removed, and the supernatant after centrifugation was further centrifuged at the centrifugal force of 10000 g for 2 hours, the precipitate was collected to obtain microparticles generated from cell vesicles derived from apoptotic A549 human lung cancer cells coating oncolytic adenoviruses.

2. Experimental Results

Figure 1A:
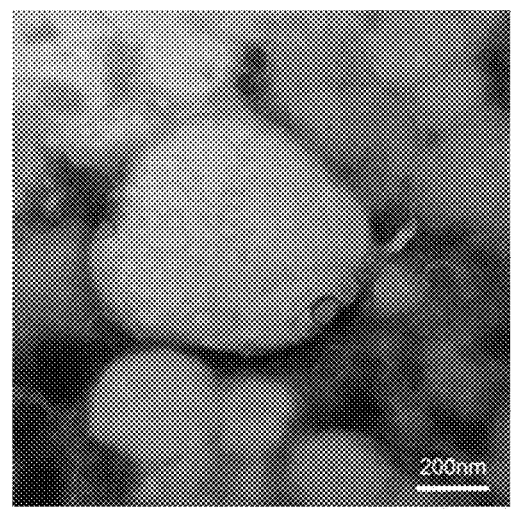
FIG. 1a is an electronic micrograph of microparticles released from cultured A549 human lung tumor cells after being treated with oncolytic adenovirus.
Figure 1B:
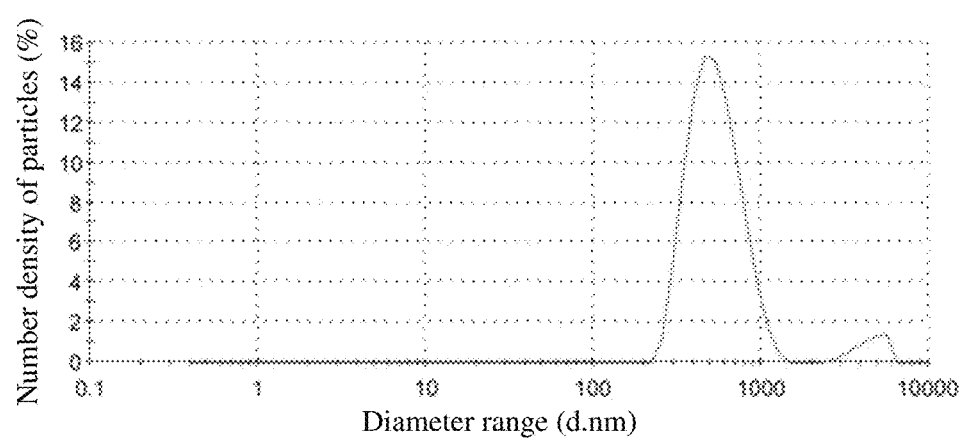
FIG. 1b is a particle size distribution graph of microparticles generated from the apoptosis of oncolytic adenovirus-induced human lung cancer cells.

The microparticles prepared above were resuspended with 1 ml of 0.9% (g/ml) physiological saline. After fixed on glass, the microparticles were observed under a transmission electron microscope. (see FIG. 1a). At the same time, the particle sizes of the microparticles were detected by Mastersizer 2000 particle size analyzer and a particle size distribution result was obtained (see FIG. 1b), the particle size distribution for the most of the microparticles in a sample was in the range of 100-1000 nm.

Example 2: Cell Vesicles Generated from the Apoptosis of Oncolytic Adenovirus-Induced Human Lung Cancer Cells Coat Oncolytic Adenovirus DNA 1. Experimental Steps A549 human lung cancer cells were cultured, so that the number of cells reached $1 \times 10^7$; $1 \times 10^8$ oncolytic adenovirus particles were added to the culture fluid; at 48th hours after administration of oncolytic adenoviruses, when the tumor cells became smaller and dimmer, microparticles (generated after cell vesicles derived from apoptotic A549 human lung cancer cells coat oncolytic adenoviruses) generated from apoptotic A549 human lung cancer cells in the supernatant of the human lung cancer cell culture fluid was collected according to the steps of Example 1.

On the one hand, the microparticles were treated with proteinase K, the membrane was lyzed and DNA molecules were separated, meanwhile oncolytic adenoviruses were treated and separated to prepare DNA molecules contained therein.

On the other hand, the microparticles obtained above were stained with PKH67 (shown in green), while adenoviruses in the microparticles were stained with PE fluorescently-labeled anti-adenovirus antibody (shown in red), and they were observed under a confocal fluorescence microscope.

As a contrast, the cell vesicles obtained from the above-mentioned A549 human lung cancer cells were stained with PKH67 (shown in green) and cell vesicles were stained with PE fluorescently-labeled anti-adenoviral antibody (shown in red), and they were observed under a confocal fluorescence microscopy.

The preparation method of the above-mentioned cell vesicles comprised the following steps: culturing tumor cells, irradiating the cells with ultraviolet rays for 30 minutes, when the tumor cells significantly became smaller and dimmer at 48th hour after UV irradiation, the supernatant of the culture liquid of mouse hepatoma cells was subjected to gradual centrifugation, that is centrifuged in sequence at the centrifugal force of 500 g, 1000 g, and 5000 g for each 10 minutes, and then centrifuged at the centrifugal force of 14000 g for 1 minute to remove cells and debris, the centrifuged supernatant was further centrifuged at the centrifugal force of 14000 g for 1 hour and precipitation was collected to get cell vesicles.

2. Experimental Results

Figure 2A:
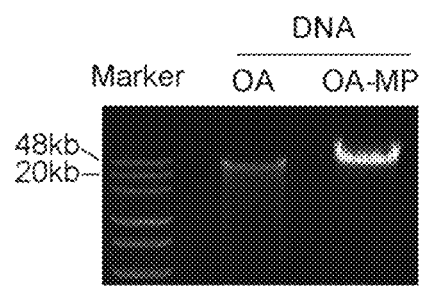
FIG. 2a shows that microparticles generated after cultured tumor cells are treated with oncolytic adenoviruses, contain oncolytic adenovirus DNA.
Figure 2B:
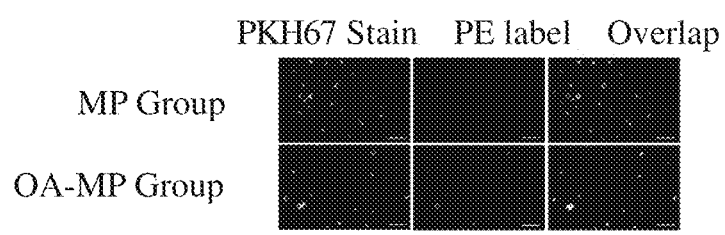
FIG. 2b shows that microparticles coating oncolytic adenoviruses. after tumor cells are treated with oncolytic adenoviruses.

Electrophoresis was carried out on DNA prepared above respectively, and the results of the electrophoresis were shown in FIG. 2a. In FIG. 2a, OA represented oncolytic adenovirus DNA, OA-MP represented DNA of microparticles which coat oncolytic adenoviruses, DNA molecular weight standard markers were at the leftmost lane. The oncolytic adenovirus genome is known to be about 23 kb in size, while the DNA electrophoresis marker contained in the microparticle sample had the same size with the known oncolytic adenovirus genome. At the same time, the results of fluorescence microscope observation were shown in FIG. 2b, PKH67 was used to stain and both MP group (cell vesicle group) and OA-MP group (microparticle group) showed green color; PE fluorescence label was used to stain anti-adenovirus antibody and MP group did not show red, and OA-MP group showed red; from the pictures provided after overlapping the stained pictures of two groups, it could be seen that in the OA-MP group green and red colocalization, indicating that the microparticles of the present invention coat oncolytic adenoviruses.

Example 3

A549 human lung cancer cells were cultured in DMEM cell culture fluid, so that the number of cells reached $1 \times 10^7$; $1 \times 10^7$ oncolytic adenoviruses were added to the culture fluid to infect human lung cancer cells; at 37° C. and 5% oxygen content, the infected tumor cells were cultured; at 48th hours after administration of oncolytic adenoviruses, when the tumor cells became smaller and dimmer, the supernatant of the human lung cancer cell culture fluid was centrifuged successively at the centrifugal force of 1000 g, 5000 g for each 10 minutes, the cells and debris were removed, and the supernatant after centrifugation was subjected to further centrifugation at the centrifugal force of 10000 g for 2 hours, precipitate was colletcted to obtain microparticles from cell vesicles derived from apoptotic A549 human lung cancer cells coating oncolytic adenoviruses.

The microparticles prepared above were resuspended with 1 ml of 0.9% (g/ml) physiological saline. After fixed on glass, the microparticles were observed under transmission electron microscope, and the particle sizes of the microparticles were detected by Mastersizer 2000 particle size analyzer and the results were the same as Example 1. Fluorescent staining is used, the results also showed that the microparticles of this example coat oncolytic adenoviruses.

Example 4

A549 human lung cancer cells were cultured in DMEM cell culture fluid, so that the number of cells reached $1 \times 10^7$; $2 \times 10^8$ oncolytic adenoviruses were added to the culture fluid to infect human lung cancer cells; at 37° C. and 5% oxygen content, the infected tumor cells were cultured; at 48th hour after administration of oncolytic adenoviruses, when the tumor cells became smaller and dimmer, the supernatant of the human lung cancer cell culture fluid was centrifuged successively at the centrifugal force of 1000 g and 5000 g for each 10 minutes, the cells and debris were removed, and the supernatant after centrifugation was subjected to further centrifugation at the centrifugal force of 10000 g for 2 hours, precipitate was collected to obtain microparticles generated from cell vesicles derived from apoptotic A549 human lung cancer cells coating oncolytic adenoviruses.

The microparticles prepared above were resuspended with 1 ml of 0.9% (g/ml) physiological saline. After fixed on glass, the microparticles were observed under a transmission electron microscope, and the particle sizes of the micropar-ticles were detected by Mastersizer 2000 particle size analyzer and the results were the same as Example 1. Fluorescent staining was used, the results also showed that the microparticles of this example coat oncolytic adenoviruses.

Example 5: Killing Effect of Oncolytic Adenovirus-Coated Microparticles on Different Tumor Cells 1. Experimental Steps The prepared oncolytic adenovirus-coated microparticles were respectively cultured with different types of human tumor cell lines which include A2780 human ovarian cancer cell line, MCF-7 human breast cancer cell line, A549 human lung cancer cell line, SNU1 human gastric cancer cell line, Caco2 human colon cancer cell line, HepG2 human hepatoma cell line, ASCP-1 human pancreatic cancer cell line, LINCap human prostate cancer cell line, as oncolytic adenovirus-coated microparticle treated groups. After 48 hours, observed the death condition of the cells. A group which treating the tumor cells with normal saline was control group, and a group which treating the tumor cells only with cell vesicles was used as cell vesicle-administered group.

Preparation of oncolytic adenovirus-coated microparticles: microparticles of the above various tumor cells were obtained according to the method of Example 1.

Microparticles of the above various tumor cells obtained according to the methods of Examples 3-4 also had the following similar tumor-killing effect.

Preparation of cell vesicles: culturing tumor cells and irradiating with ultraviolet rays for 30 minutes. After 48 hours of UV irradiation, when tumor cells became obvious smaller and dimmer, centrifuging the supernatant of the mouse hepatoma cell culture fluid successively at the centrifugal force of 500 g, 1000 g and 5000 g for each 10 minutes, followed by centrifugation at the centrifugal force of 14000 g for 1 minute to remove cells and debris, and subjecting the supernatant after centrifugation to further centrifugation at the centrifugal force of 10000 g for 1 hour, collecting precipitate to obtain cell vesicles.

2. Experimental Results

Figure 3:
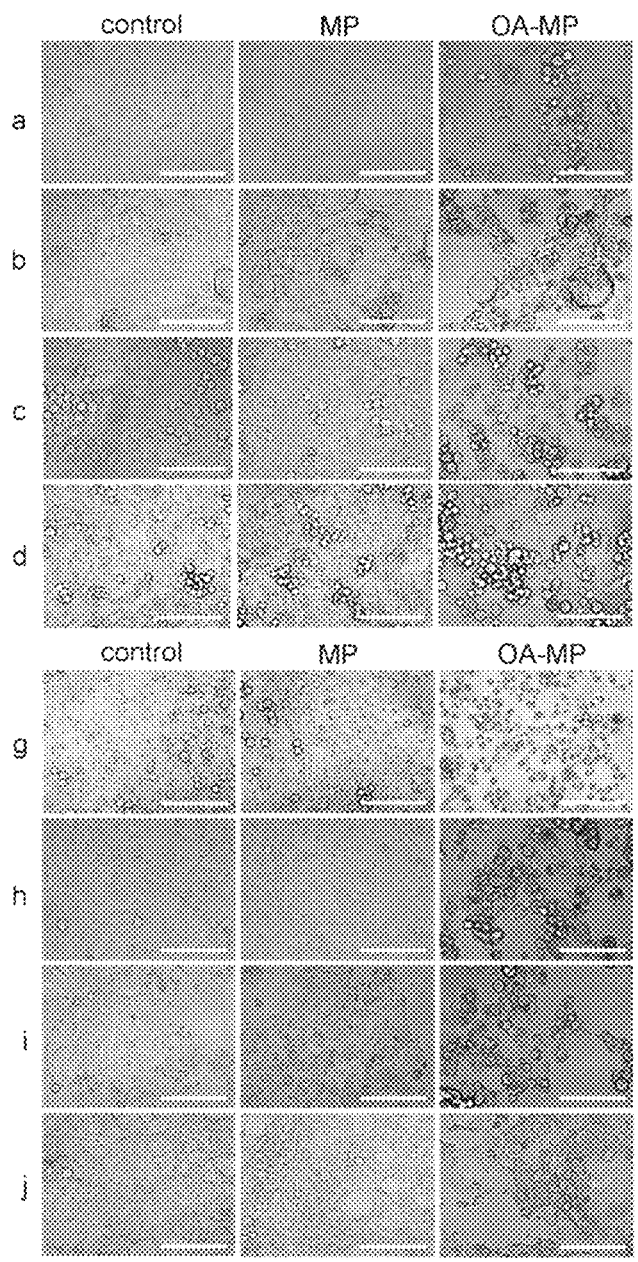
FIG. 3 shows graph of the effect of oncolytic adenovirus-coated microparticles killing variety of human tumor cells. In the graph, a, b, c and d represents A2780 human ovarian cancer cell line, MCF-7 human breast cancer cell line, A549 human lung cancer cell line and SNU1 human gastric cancer cell line respectively; g, h, i and j represents Caco2 human colon cancer cell line, HepG2 human hepatoma cell line, ASCP-1 human pancreatic cancer cell line, LINCap human prostate cancer cell line respectively.

Tumor cells were treated as above, and after 48 hours, the cells in each group were observed under an inverted phase contrast microscope. The cells in control group and MP group (only administration of cell vesicles) showed an adherent growth state; while cells in OA-MP treated group (administration of oncolytic adenovirus-coated microparticles) were detached from adherence and showed a dead state (FIG. 3), indicating that the microparticles coating oncolytic adenoviruses have discernible cytotoxic effect on tumor cells.

Example 6: Microparticles Coating Oncolytic Adenoviruses have No Toxic Side Effects on Body 1. Experimental Steps Mice were tail vein injected with phosphate buffered saline (PBS), cellular vesicles (MP), oncolytic adenoviruses (OA) and oncolytic adenovirus-coated microparticles (OA-MP) one time a day respectively, total 5 times, the mice were killed on the 6th day, and then the content of glutamic-pyruvic transaminase (ALT) and creatinine (CRE) were detected in the serum of the mice. The microparticles and cell vesicles used in this example were the same as those in Example 2. Microparticles used in Examples 3-4 also had no toxic side effects on body.

2. Experimental Results

Figures 4A, 4B:
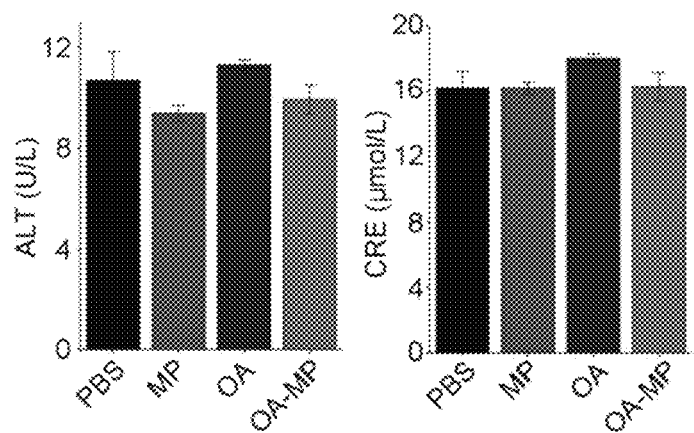
FIG. 4a and FIG. 4b show the content of alanine transaminase (ALT) and creatinine (CRE) in the serum of mouse in each group, which shows that the oncolytic adenovirus-coated microparticles have no obvious toxic side effects on the body.

As can be seen from FIG. 4a and FIG. 4b, compared with mouse injected with PBS or single cell vesicles in control group, there was no obvious change in the content of glutamic-pyruvic transaminase and creatinine for mouse injected with microparticles generated from cell vesicles coating oncolytic adenoviruses in treated group.

Example 7: Microparticles Coating Oncolytic Adenoviruses Inhibit Tumor Growth and Extend Survival Time of Tumor-Bearing Mice 1. Experimental Steps Nude mice were subcutaneously injected with $1 \times 10^6$ A549 human lung cancer cells. After 5 days, cell vesicles (MP), oncolytic adenoviruses (OA) and oncolytic adenovirus-coated microparticles (OA-MP) were directly injected to a tumor inoculation site once for 3 days, total for 5 times. Observe the effect of subcutaneous tumor growth. The number of cell vesicles and microparticles for each injection were the same of $2 \times 10^6$, the amount of adenoviruses was $2 \times 10^6$.

Nude mice were intraperitoneally injected with $5 \times 10^6$ A549 human lung cancer cells. After 3 days, PBS solution, single oncolytic adenoviruses (OA), single cell vesicles (MP) and oncolytic adenovirus-coated microparticles (OA-MP) were directly intraperitoneally injected respectively once for 3 days, total for 5 times. Observe the mice survival time. The number of cell vesicles and microparticles for each injection were the same of $3 \times 10^6$, the amount of adenovirus was $3 \times 10^6$.

Nude mice were intraperitoneally injected with $5 \times 10^6$ A2780 human ovarian cancer cells. After 3 days, cell vesicles (MP), oncolytic adenoviruses (OA) and oncolytic adenovirus-coated microparticles (OA-MP) were intraperitoneally injected respectively once for 3 days, total for 7 times. Observe the intraperitoneal tumor growth. The number of cell vesicles and microparticles for each injection were the same of $3 \times 10^6$, the amount of adenovirus was $3 \times 10^6$.

In this example, the method for preparing microparticles and cell vesicles was the same as Example 2. Using the preparation methods of Examples 3-4 would also obtain the following similar effects.

2. Experimental Results

Figure 5A:
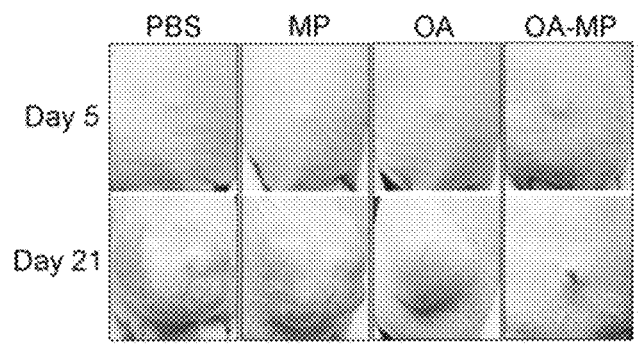
FIG. 5a shows the tumor volume of A549 tumor-bearing mouse after being treated with phosphate buffered saline (PBS), cell vesicles (MP), oncolytic adenoviruses (OA), and oncolytic adenovirus-coated microparticles (OA-MP) respectively on the 5th day and 21th day.
Figure 5B:
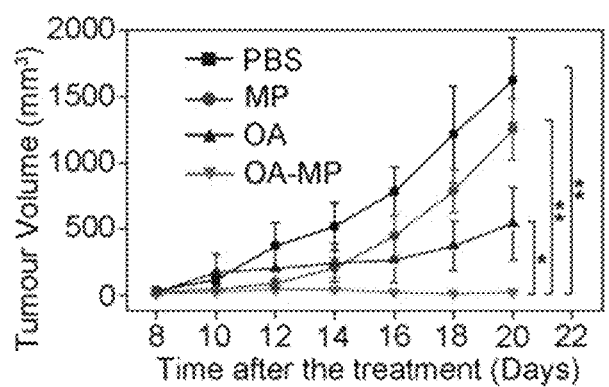
FIG. 5b shows the tumor volume of A549 tumor-bearing mouse detected at different time points after the mouse is treated with PBS, MP, OA, OA-MP respectively.

Nude mice were subcutaneously injected with A549 tumor cells, and tumor nodules began to grow on the 5th day. However, after the treatment of oncolytic adenoviruses-coated microparticles, the tumor growth was significantly inhibited, and the tumor volume was significantly smaller than that of the other control groups (FIG. 5a showed the size of tumor volumes on day 5 and day 21 and FIG. 5b showed tumor volumes were detected at different time points), i.e., compared to the group where only oncolytic adenoviruses were administrated and the group where single cell vesicles were administrated, the growth of subcutaneously A549 tumor of nude mice in group where oncolytic adenoviruses-coated microparticles were administrated, can be significantly inhibited.

Figure 5C:
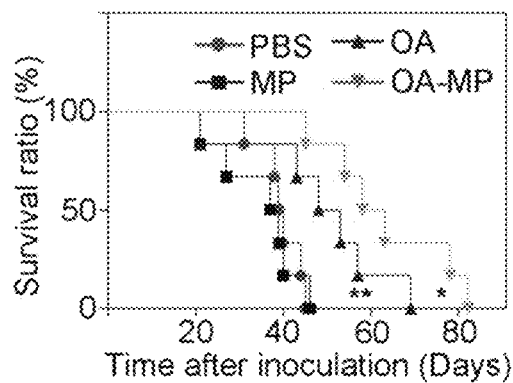
FIG. 5c shows the survival rate of A549 tumor-bearing mice after being treated with PBS, MP, OA respectively.

After nude mice were intraperitoneally injected with A549 tumor cells, the treatment of oncolytic adenovirus-coated microparticles significantly prolonged the lifetime of tumor-bearing mice. Compared to the group where single oncolytic adenoviruses were administrated, $p<0.05$ (FIG. 5c showed the survival rate of tumor-bearing mice after being treated with PBS, MP, OA, and OA-MP), that is, compared to the group where single oncolytic adenoviruses were administered and the group where single cell vesicleses were administered, the lifetime of tumor-bearing mice in the group where oncolytic adenovirus-coated microparticles were administrated can be significantly prolonged.

Figure 5D:
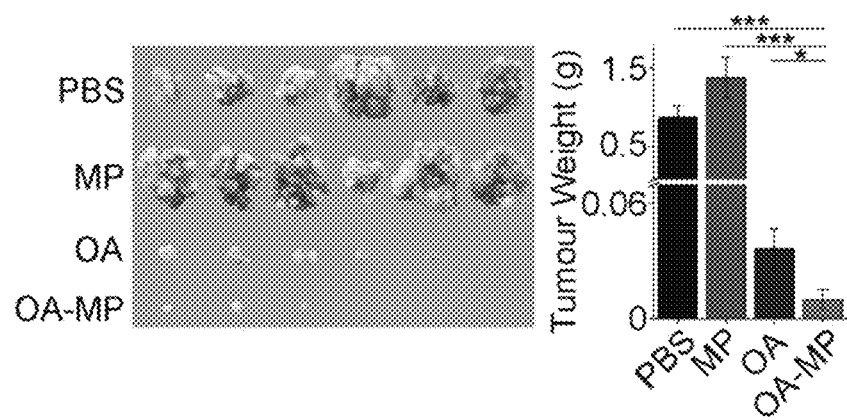
FIG. 5d shows the growth of A2780 tumor in nude mice after being treated with PBS, MP, OA and OA-MP respectively.

After nude mice were intraperitoneally injected with A2780 tumor cells, then were treated with phosphate buffered saline (PBS), single cell vesicles (MP), single oncolytic adenoviruses (OA), and oncolytic adenovirus-coated microparticles (OA-MP) respectively, after 30 days, the tumor size and weight were detected and the results were shown in FIG. 5*d*, i.e. compared to the group where only oncolytic adenoviruses were administered and the group where single cell vesicles were administered, the treatment of the group where oncolytic adenovirus-coated microparticles were administrated can significantly inhibited the growth of ovarian tumor. Compared to the single oncolytic adenovirus group (see FIG. 5*d*), $p<0.05$.

What is claimed is:

1. A method for preparing an oncolytic virus formulation, comprising mixing oncolytic viruses and tumor cells in a ratio of 1:1 to 20:1 so as to infect tumor cells, and culturing the infected tumor cells to induce apoptosis at 37° C. and 5% oxygen content, collecting microparticles released from the apoptotic tumor cells within 48-72 hours, wherein the microparticles are the oncolytic virus formulation generated after the oncolytic virus is coated with cell vesicles;

wherein the collection of the microparticles released from the apoptotic tumor cells comprises removing the tumor cells and debris by an ultracentrifuge at a centrifugal force of not more than 5000 g, and collecting the microparticles by the ultracentrifuge at a centrifugal force of 10000 g.

2. The method according to claim 1, wherein the tumor cells include cells of ovarian cancer, breast cancer, lung cancer, gastric cancer, colon cancer, liver cancer, pancreatic cancer or prostate cancer.

\* \* \* \* \*